United States Patent [19]
Moore et al.

[11] Patent Number: 5,855,562
[45] Date of Patent: Jan. 5, 1999

[54] SUCTION CONTROL VALVE

[75] Inventors: David R. Moore, Oceanside; Thomas C. Loescher, Encinitas, both of Calif.

[73] Assignee: Hudson Respiratory Care Inc., Temecula, Calif.

[21] Appl. No.: 779,712

[22] Filed: Jan. 7, 1997

[51] Int. Cl.$^6$ ....................................................... A61M 1/00
[52] U.S. Cl. .............................. 604/119; 604/902; 433/91
[58] Field of Search ..................... 604/118, 119, 604/313, 315, 902; 137/533.17; 15/407, 48; 251/142, 148, 152, 205; 433/91

[56] References Cited

U.S. PATENT DOCUMENTS

| | | |
|---|---|---|
| 3,517,669 | 6/1970 | Buono et al. . |
| 3,834,388 | 9/1974 | Sauer . |
| 3,902,500 | 9/1975 | Dryden . |
| 3,911,919 | 10/1975 | Raitto . |
| 3,937,220 | 2/1976 | Coyne . |
| 3,991,762 | 11/1976 | Radford . |
| 4,300,550 | 11/1981 | Gandi et al. . |
| 4,836,199 | 6/1989 | Palmer . |
| 4,857,047 | 8/1989 | Amoils ................................ 604/119 X |
| 5,073,164 | 12/1991 | Hollister et al. . |
| 5,125,893 | 6/1992 | Dryden . |
| 5,139,018 | 8/1992 | Brodsky et al. . |
| 5,354,267 | 10/1994 | Niermann et al. . |

*Primary Examiner*—Ronald Stright, Jr.
*Assistant Examiner*—N. Kent Gring
*Attorney, Agent, or Firm*—Knobbe, Martens, Olson & Bear, LLP

[57] ABSTRACT

A suction control valve comprising a valve housing defining a cavity and including an inlet port for being connected to a suction tube, an outlet port for being connected to a suction source, and a suction control port for creating a suction across the cavity from the inlet port to the outlet port when the suction control port is closed. The valve preferably includes a bacteria filter secured in the cavity for preventing exposure of the suction control port to bacteria entering the inlet port. A splash guard extends along the cavity for preventing liquid from contacting the bacteria filter or from reaching the suction control port. A suction control port guard is selectively movable to prevent accidental closure of the suction control port.

28 Claims, 3 Drawing Sheets

SUCTION CONTROL VALVE

BACKGROUND OF THE INVENTION

A suction catheter is used with an endotracheal tube for irrigating a patient's lungs to remove lung secretions. The suction catheter assembly includes a catheter surrounded by an elongated transparent flexible bag attached to an adapter for connection to the endotracheal tube. The opposite end of the catheter is connected to a suction machine or vacuum source by a suction control valve operated by a therapist or physician for selectively suctioning the patient. Examples of suction catheter assemblies are shown in U.S. Pat. Nos. 3,902,500, 5,125,893 and 3,991,762, the descriptions of which are incorporated herein by reference. In U.S. Pat. Nos. 4,569,344, 4,696,296, 4,836,199 and 4,872,579, there are disclosed suction catheter assemblies which include suction control valves by which an operator may selectively suction a patient as described in the aforesaid patents. However, such valves are costly to manufacture, assemble and maintain, and thus increase patient and hospital costs for procedures requiring the use of such apparatus.

SUMMARY OF THE INVENTION

The suction control apparatus of the present invention is relatively inexpensive to manufacture and assemble and easy to operate. The suction control device includes a fluid barrier or splash guard for preventing exposure of a user to fluids suctioned through the device. The device also includes a suction control port guard for preventing inadvertent closure of the suction control port and avoiding accidental suction. The device also preferably includes a bacteria filter. These as well as other features and advantages of the invention will be evident from the following detailed description.

DETAILED DESCRIPTION OF THE PREFERRED EMBODIMENT

Figure 1:
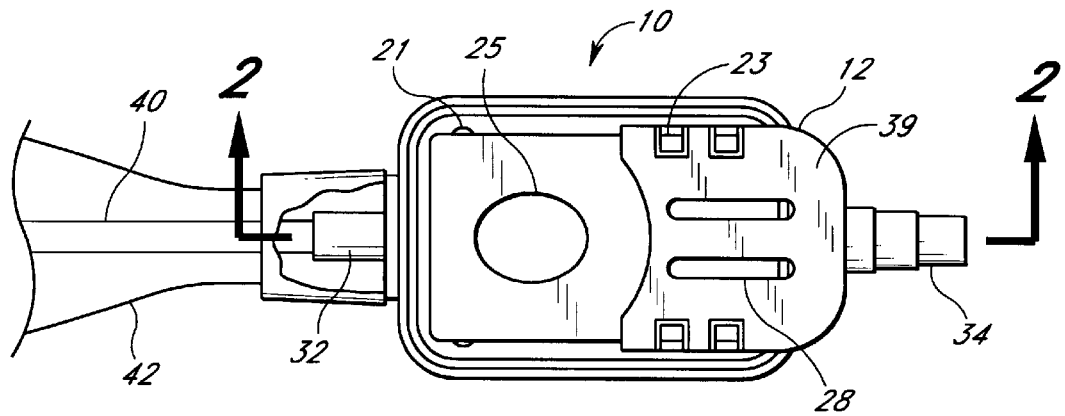
FIG. 1 is a top view of the suction control valve.
Figure 2:
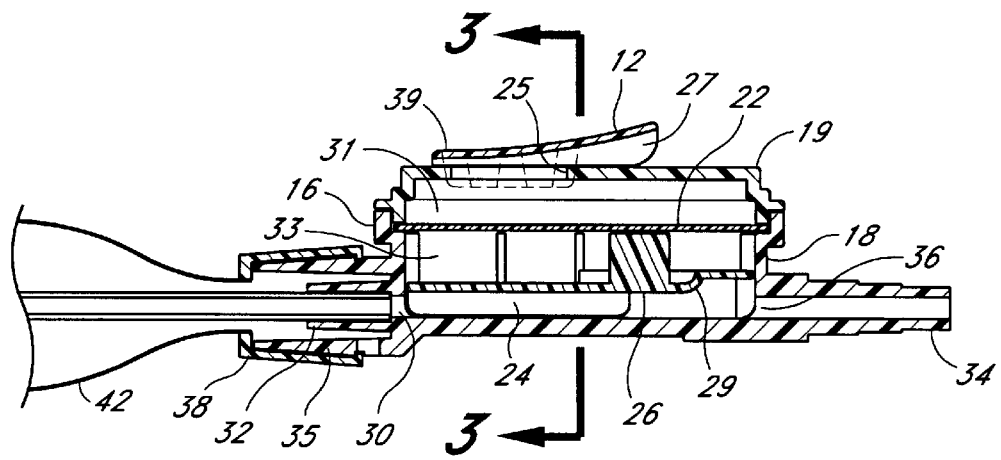
FIG. 2 is a side sectional elevation of the suction control valve taken along lines 2—2 of FIG. 1.
Figure 3:
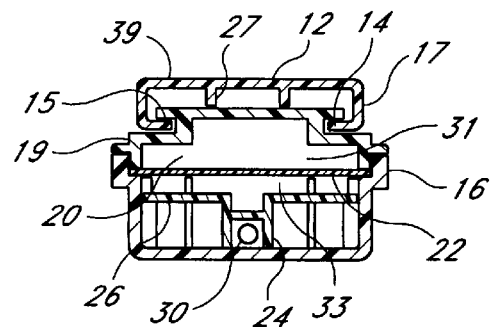
FIG. 3 is a sectional view of the suction control valve taken along lines 3—3 of FIG. 2.

The preferred embodiment of the suction control valve of the invention is illustrated in FIGS. 1–3. The valve 10 includes a valve housing 16 defining an interior cavity 20 with which inlet port 30 and outlet port 36 communicate. The inlet port 30 is connected to catheter 40 which is used for suctioning a patient as disclosed in the aforesaid prior patents, and need not be further described herein. The catheter 40 is secured to an inlet port fitting 32. The end of bag or sheath 42 is secured between cap 38 and enlarged fitting 35 which is coaxial with inlet port fitting 32. The inlet port fitting 32 and enlarged fitting 35 are integral components of the valve housing, and formed as part of the lower housing member 18. Outlet pipe 34 is also an integral component of the lower housing member 18 for being secured to a suction or vacuum source, not shown.

An upper housing member 19 is secured to the lower housing member 18 to form the valve housing 16 and define the interior cavity 20. A suction control port 25 is formed in the top plate or surface of the upper housing member 19, which control port communicates with the interior cavity 20. The peripheral edge of filter 22 is secured between the engaging surfaces of the upper and lower housing members. This is more specifically seen in FIGS. 2 and 3 showing the outer edge of the filter 22 sandwiched between the mating surfaces of the upper and lower housing members. Preferably, the filter is ultrasonically welded to one or both of the housing members at the time the apparatus is assembled. It will be observed that the filter extends entirely across the cavity 20 and separates the cavity into upper 31 and lower 33 chambers. Suction control port 25 communicates with the upper cavity chamber 31. The presence of filter 22 precludes exposure of the upper chamber 31 to the inlet port 30 or outlet port 36 which communicate with the lower cavity chamber 33. As a result, fluid entering the cavity 20 via inlet port 30 is restricted to the lower cavity chamber 33 by the filter 22 thereby preventing potential exposure of a user or operator from fluid, micro aerosols and microorganisms in the fluid drawn into the chamber via suction control port 25.

Another preferred feature of the apparatus shown is a splash guard 26 which extends across the lower cavity chamber 33 above the inlet and outlet ports 30 and 36, respectively. The purpose of the splash guard 26 is to prevent particles of fluid traveling along the interior of the lower cavity chamber between the inlet and outlet ports from splashing onto the filter 22 which would wet the filter and reduce it's effectiveness against preventing passage of microorganisms and would cause an unacceptable amount of negative suction pressure to the inlet port 30 when it is not desired. The splash guard 26 is shown in a preferred embodiment which comprises a plate 29 extending partially across the length of the lower cavity chamber 33, and a tunnel member 24 having a top and sides which extend to the bottom surface of the interior cavity along a substantial length, preferably over half of the distance from the inlet port 30 to the outlet port 36. It will also be observed that neither the tunnel member 24 nor the plate 29 extend the entire length of the distance between the two ports, although they overlap somewhat. Moreover, the width of the plate also preferably extends substantially entirely across the width of the lower cavity chamber. Because the two splash guard components overlap, and because the tunnel 24 substantially encloses or surrounds a portion of the fluid flow path from the inlet port 30, the splash guard substantially prevents the filter member from being contacted by the fluid passing between the inlet and outlet ports. However, it should also be understood that different shapes and dimensions of the splash guard including the plate and tunnel components may be used, and although those shown are preferred, the invention is not to be so limited. For example, the splash guard may be entirely a plate, or a tunnel, of any desired shape.

Another important feature of the suction control valve assembly of the present invention is a suction control port guard 12. The guard is movable along a substantial portion of the length of the upper surface of the valve housing between a first position in which the guard overlies the suction control port 25, and a second position in which the suction control port is substantially fully exposed. The purpose of the suction control port guard is to prevent accidental occlusion or partial occlusion of the suction control port which would cause an unacceptable amount of negative suction pressure to the inlet port 30 when it is not desired. When use of the apparatus is desired, an operator can readily move the suction control port guard to fully expose the suction control port, and when not in use, the guard is positioned to overlie the port.

The suction control guard preferably comprises an assembly having features including one or more support ribs 27 which act as spacers for maintaining a separation between the cover plate 39 and the suction control port 25. A guide support member 17 is also positioned on each side of the assembly and extends downwardly from the cover plate 39 to guide flanges 14 along each side of the housing. The flanges extend into slots or tracks formed along the upper side of the upper housing member 19. Thus, the suction control guard is aligned and conveniently moved along the track or slot between the first and second positions. The cover plate 39 is also preferably provided with one or more vents 28 which further ensure that sufficient ambient air can be drawn into the suction control port 25 when the guard is positioned to overlie the port, and to prevent any reduction in the amount of air entrained into the port, which could create a negative pressure within the suction control valve. The assembly may also be provided with one or more detents 21 or similar components or features, preferably positioned adjacent to or near the track or slot 15 and cooperating with recesses along one or both guides 14 for receiving the detents whereby the guard may be temporarily locked in an open and/or closed position relative to the suction control port to prevent the guard member from inadvertently sliding from one position to another if the valve assembly is moved or tilted.

Figure 4:
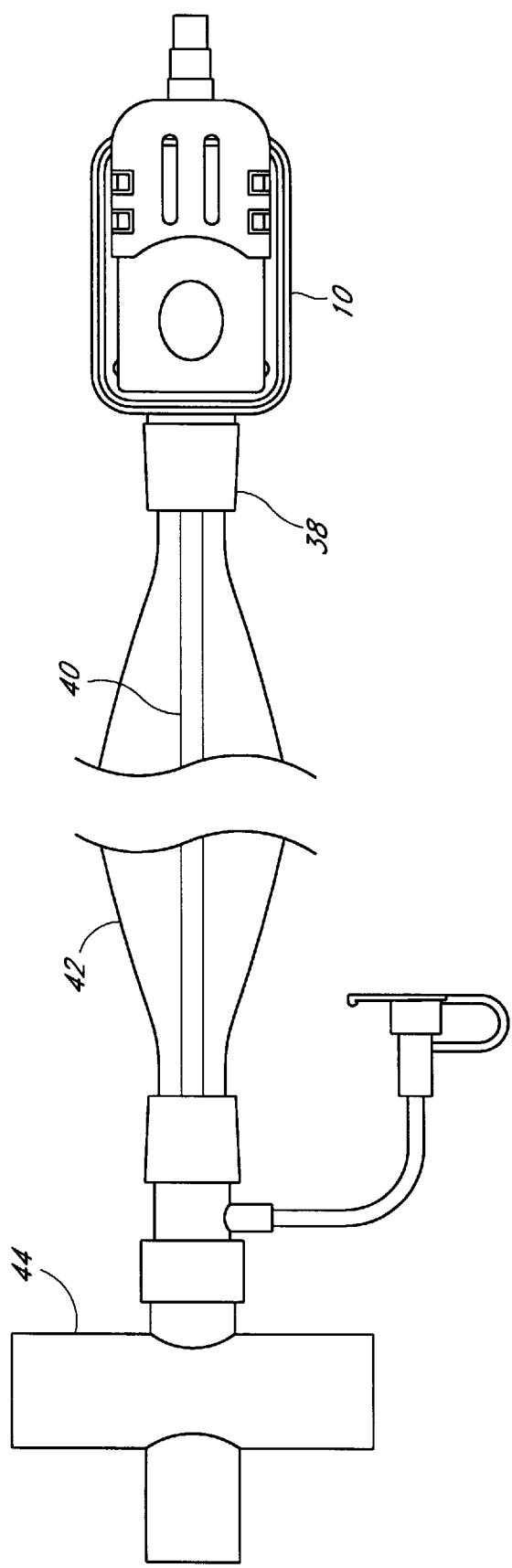
FIG. 4 illustrates a partial view of a suction catheter assembly incorporating the suction control valve of the present invention.

A suction catheter assembly is illustrated in FIG. 4 showing the position of the suction control valve 10 of the present invention relative to other components of the assembly. For example, at the proximal end of the apparatus is an adapter 44, sometimes referred to as an adapter tee, for being connected to a ventilator and source of irrigation fluid, saline solution, and to an endotracheal tube or other patient circuit. When it is desired to suction a patient, the operator will slide the suction control port guard 12 to the position illustrated in FIG. 1 thereby exposing the suction control port 25. The operator then grasps the patient connector 44 with one hand and advances the catheter 40 to the desired depth within the patient. Typically, the catheter is provided with numerals indicating the length of the catheter tube that extends past or beyond the patient connector. The operator then intermittently controls the suction by placing a thumb over the suction valve port and gently withdraws the catheter. When the procedure is complete, the catheter is fully retracted so that it lies outside of adaptor 44. The catheter may then be flushed by applying suction and slowly instilling solution into the irrigation port. When suctioning is not to be used, the guard is positioned to overlie the suction control port.

Figure 5:
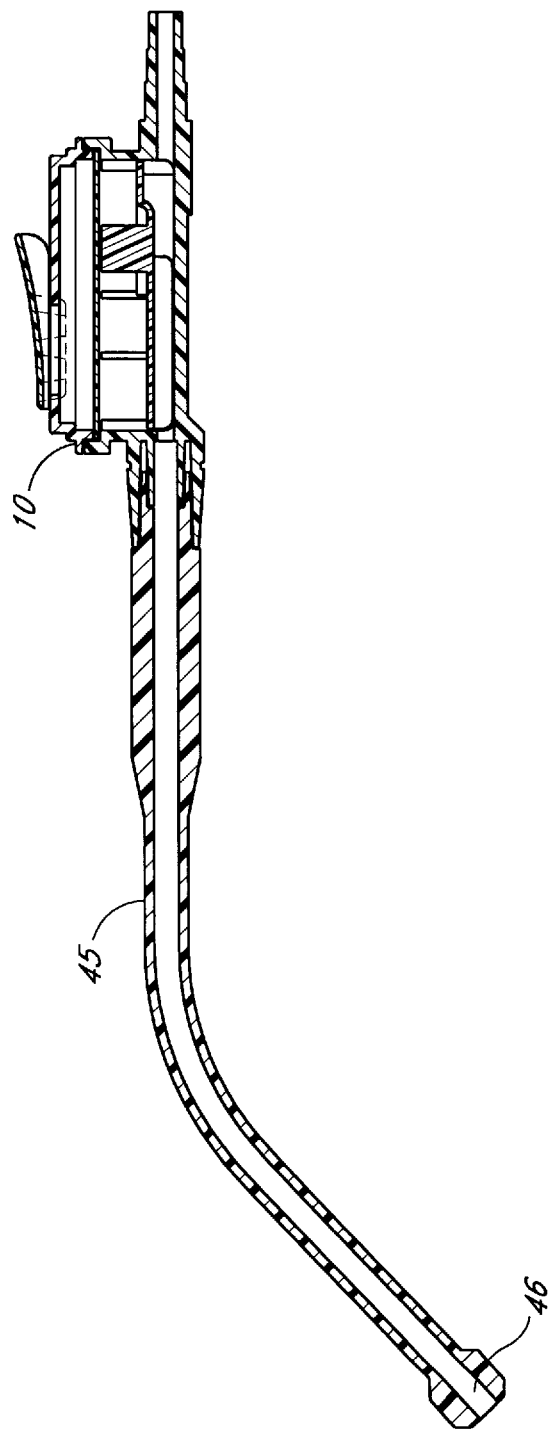
FIG. 5 illustrates a side sectional view of an elongated curved tube incorporating the suction control valve of the present invention.

FIG. 5 illustrates an oral or body cavity suction assembly or aspirator showing the position of the suction control valve 10 of the present invention relative to other components of the assembly. By way of example, attached to the suction control valve 10 is a cylindrical tube 45, sometimes referred to as a Yanker suction tube, for insertion into a cavity for the removal of secretions. Typically, the cylindrical tube 45 is of a length and shape so that it can be inserted deep into the oral cavity to a level just above the laryngeal opening. When it is desired to suction a patient, the operator will slide the suction control port guard 12 to the position illustrated in FIG. 1 thereby exposing the suction control port 25. The operator positions the end 46 of the cylindrical tube 45 to the location of fluids or secretions to be aspirated. The operator intermittently controls the suction by placing a thumb over the suction valve port and gently suctions the patient. When the procedure is complete, the cylindrical tube is removed from the patient. The cylindrical tube 45 may then be cleaned by suctioning a solution into the distal opening 46 of the cylindrical tube 45. When suctioning is not to be used, the guard is positioned to overlie the suction control port.

In addition to the above-described assemblies incorporating the valve of the invention, it may be used for controlling suction in a number of other medical or dental suction appliances, syringes and the like. These as well as other features and embodiments within the purview of the invention will be evident to those skilled in the art.

What is claimed is:

1. A suction control valve comprising:
   a valve housing defining a cavity therein said housing including an inlet port for being connected to a suction tube, an outlet port for being connected to a suction source, and a suction control port cooperating therewith for creating a suction across said cavity from said inlet port to said outlet port when said suction control port is closed;
   a bacteria filter secured along the interior perimeter of said valve housing for preventing exposure of said suction control port to bacteria entering said inlet port; and
   a splash guard extending along said cavity between said inlet port and said outlet port for substantially preventing liquid passing through said cavity from said inlet port to said outlet port from contacting said bacteria filter.

2. A suction control valve of claim 1 including a suction control port guard selectively movable from a first position which substantially prevents closure of said suction control port to a second position which exposes said suction control port for selective closure thereof.

3. A suction control valve of claim 2 wherein said suction control port guard comprises a movable cover plate and a spacer member for maintaining a space between said cover plate and said suction control port.

4. A suction control valve of claim 3 wherein said suction control port guard is movably secured on said valve housing.

5. A suction control valve of claim 4 wherein said valve housing includes a track and said suction control port guard includes a guide member movable along said track.

6. A suction control valve of claim 3 wherein said spacer member comprises ribs extending between said cover plate said valve housing.

7. A suction control valve of claim 6 including a detent cooperating with said track for limiting the movement of said suction control port guard in said first position.

8. A suction control valve of claim 7 including a guide member secured to said cover plate and slidably engaged in said track for movement therealong.

9. A suction control valve of claim 2 wherein said suction control port guard is movably secured on said valve housing.

10. A suction control valve of claim 9 wherein said valve housing includes a track and said suction control port guard includes a guide member movable along said track.

11. A suction control valve of claim 10 wherein said valve housing includes a top surface with said suction control port positioned thereon, and wherein said suction control port guard is movable along a plane substantially parallel with said top surface.

12. A suction control valve of claim 10 wherein said valve housing includes restraining means cooperating with said suction control port guard for limiting the movement thereof when said guard is in said first position.

13. A suction control valve of claim 2 wherein said valve housing includes a top surface with said suction control port positioned thereon, and wherein said suction control port guard is movable along a plane substantially parallel with said top surface.

14. A suction control valve of claim 2 wherein said suction control port guard is substantially oversized relative to the perimeter of said suction control port opening.

15. A suction catheter assembly comprising:
    an elongated suction catheter having a distal end for performing suction procedure, and a proximal end secured to a suction control valve; and
    a suction control valve of claim 1, wherein said proximal end of said suction catheter is secured to said valve housing adjacent to said inlet port.

16. A suction catheter assembly of claim 15 including an adapter for attaching said assembly to a ventilator adjacent to said distal end of said catheter, and a flexible sheath for substantially enclosing said catheter between said adapter and said suction control valve.

17. A suction catheter assembly of claim 16 including a suction control port guard selectively movable from a first position which substantially prevents closure of said suction control port to a second position which exposes said suction control port for selective closure thereof.

18. An aspirator assembly comprising:
    an elongated suction tube having a distal end for performing suction procedure, and a proximal end secured to a suction control valve; and
    a suction control valve of claim 1, wherein said proximal end of said suction tube is secured to said valve housing adjacent to said inlet port.

19. A suction assembly of claim 18 including a suction control port guard selectively movable from a first position which substantially prevents closure of said suction control port to a second position which exposes said suction control port for selective closure thereof.

20. A suction control valve comprising:
    a valve housing defining a cavity therein said housing including an inlet port for being connected to a suction tube, an outlet port for being connected to a suction source, and a suction control port cooperating therewith for creating a suction across said cavity from said inlet port to said outlet port when said suction control port is closed; and
    a splash guard extending along substantially the entire length of said cavity between said inlet port and said outlet port for substantially preventing liquid passing through said cavity from said inlet port to said outlet port from entering said suction control port.

21. A suction control valve of claim 20 including a suction control port guard selectively movable from a first position which substantially prevents closure of said suction control port to a second position which exposes said suction control port for selective closure thereof.

22. A suction control valve of claim 21 wherein said suction control port guard comprises a movable cover plate and a spacer member for maintaining a space between said cover plate and said suction control port.

23. A suction control valve of claim 22 wherein said spacer member comprises ribs extending between said cover plate said valve housing.

24. A suction control valve of claim 21 wherein said suction control port guard is movably secured on said valve housing.

25. A suction control valve of claim 24 wherein said valve housing includes a track and said suction control port guard includes a guide member movable along said track.

26. A suction control valve of claim 24 wherein said valve housing includes a top surface with said suction control port positioned thereon, and wherein said suction control port guard is movable along a plane substantially parallel with said top surface.

27. A suction control valve of claim 24 wherein said valve housing includes restraining means cooperating with said suction control port guard for limiting the movement thereof when said guard is in said first position.

28. A suction control valve of claim 20 wherein said suction control port guard is substantially oversized relative to the perimeter of said suction control port opening.

* * * * *